United States Patent
Higuchi et al.

(10) Patent No.: US 11,019,993 B2
(45) Date of Patent: Jun. 1, 2021

(54) OCT DATA PROCESSING DEVICE AND NON-TRANSITORY COMPUTER-READABLE MEDIUM STORING COMPUTER-READABLE INSTRUCTIONS

(71) Applicant: NIDEK CO., LTD., Gamagori (JP)

(72) Inventors: Yukihiro Higuchi, Okazaki (JP); Tetsuya Kano, Kariya (JP); Ryosuke Shiba, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 108 days.

(21) Appl. No.: 16/281,441

(22) Filed: Feb. 21, 2019

(65) Prior Publication Data
US 2019/0274541 A1    Sep. 12, 2019

(30) Foreign Application Priority Data

Mar. 6, 2018    (JP) .............................. JP2018-040238

(51) Int. Cl.
| | |
|---|---|
| *A61B 3/10* | (2006.01) |
| *A61B 3/14* | (2006.01) |
| *A61B 5/00* | (2006.01) |
| *A61B 3/00* | (2006.01) |

(52) U.S. Cl.
CPC ............ *A61B 3/102* (2013.01); *A61B 3/0058* (2013.01); *A61B 3/14* (2013.01); *A61B 5/004* (2013.01); *A61B 5/0066* (2013.01)

(58) Field of Classification Search
CPC .. A61B 3/102; A61B 3/10; A61B 3/12; A61B 3/14; A61B 5/0062; A61B 5/0066
USPC ................ 351/206, 246, 221, 210, 205, 200
See application file for complete search history.

(56) References Cited

U.S. PATENT DOCUMENTS

| | | | |
|---|---|---|---|
| 2017/0209037 A1 | 7/2017 | Sumiya | |
| 2017/0231484 A1* | 8/2017 | Komine | ............... A61B 3/0058 |
| | | | 351/206 |
| 2017/0325679 A1 | 11/2017 | Ishiai et al. | |

FOREIGN PATENT DOCUMENTS

| | | |
|---|---|---|
| EP | 3305175 A2 | 4/2018 |
| JP | 2016-013210 A | 1/2016 |

OTHER PUBLICATIONS

Jul. 22, 2019 Extended European Search Report issued in European Application No. 19158247.7.

* cited by examiner

*Primary Examiner* — Hung X Dang
(74) *Attorney, Agent, or Firm* — Oliff PLC

(57) ABSTRACT

An OCT data processing device includes a processor that performs acquiring three-dimensional OCT data. The three-dimensional OCT data is OCT data of a tissue of a subject's eye acquired by an OCT device and is obtained by irradiating measurement light on a two-dimensional measurement region. The two-dimensional measurement region extends in a direction intersecting an optical axis of the measurement light. The processor further preforms setting a line pattern, from among a plurality of types of line pattern, with respect to the two-dimensional measurement region for which the three-dimensional OCT data is obtained, at least one of an arrangement, a number, or a shape of one or more lines being different for the plurality of types of line pattern, and extracting, from the three-dimensional OCT data, a two-dimensional tomographic image of a cross section intersecting each of the one or more lines of the set line pattern.

9 Claims, 5 Drawing Sheets

OCT DATA PROCESSING DEVICE AND NON-TRANSITORY COMPUTER-READABLE MEDIUM STORING COMPUTER-READABLE INSTRUCTIONS

CROSS REFERENCE TO RELATED APPLICATION

This application is based upon and claims the benefit of priority of Japanese Patent Application No. 2018-040238 filed on Mar. 6, 2018, the contents of which are incorporated herein by reference in its entirety.

BACKGROUND

The present disclosure relates to an OCT data processing device that processes OCT data acquired on the basis of the principle of optical coherence tomography (OCT), and a non-transitory computer-readable medium storing computer-readable instructions.

Conventionally, an OCT device is known that acquires OCT data (such as a tomographic image, for example) of a test subject, using reflected light of measurement light, and reference light. For example, by changing a scanning position of measurement light (namely, a scan pattern of the measurement light), a known OCT device can acquire a tomographic image of an ocular fundus using various methods, such as macula line photography, macula map photography, papilla map photography, and the like.

SUMMARY

In the above conventional OCT device, of a plurality of scan patterns, a scan pattern executed by the OCT device in actuality needs to be set in advance in accordance with a medical condition and the like of a subject's eye. Further, after completing photography using a scan pattern, a user (a doctor or the like, for example) may desire to verify a result photographed using another scan pattern. In this type of case, it is necessary to perform the photography using the OCT device again. Thus, with the conventional device, it may be difficult to appropriately acquire information relating to a tissue of the test subject.

Embodiments of the broad principles derived herein provide an OCT data processing device and a non-transitory computer-readable medium storing computer-readable instructions for appropriately acquiring information relating to a tissue of a test subject.

Embodiments provide an OCT data processing device that includes a processor preforms processes including: acquiring three-dimensional OCT data, the three-dimensional OCT data being OCT data of a tissue of a subject's eye acquired by an OCT device, the OCT device comprises an OCT light source, a branching optical element, an irradiation optical system, a multiplexing optical element, and a photodetector, the branching optical element dividing light emitted from the OCT light source into measurement light and reference light, the irradiation optical system irradiating the measurement light divided by the branching optical element onto the tissue, the multiplexing optical element combining the measurement light reflected by the tissue and the reference light divided by the branching optical element and cause the measurement light and the reference light to interfere with each other, the photodetector detecting an interference signal by receiving interference light generated by the multiplexing optical element, the three-dimensional OCT data being three-dimensional OCT data obtained by irradiating the measurement light on a two-dimensional measurement region, the two-dimensional measurement region extending in a direction intersecting an optical axis of the measurement light; setting a line pattern, from among a plurality of types of line pattern, with respect to the two-dimensional measurement region for which the three-dimensional OCT data is obtained, at least one of an arrangement, a number, or a shape of one or more lines being different for the plurality of types of line pattern; and extracting, from the three-dimensional OCT data, a two-dimensional tomographic image of a cross section intersecting each of the one or more lines of the set line pattern.

Embodiments provide a non-transitory computer-readable medium storing computer-readable instructions that, when executed by a processor of an OCT data processing device, cause the device to perform processes including: acquiring three-dimensional OCT data, the three-dimensional OCT data being OCT data of a tissue of a subject's eye acquired by an OCT device, the OCT device comprises an OCT light source, a branching optical element, an irradiation optical system, a multiplexing optical element, and a photodetector, the branching optical element dividing light emitted from the OCT light source into measurement light and reference light, the irradiation optical system irradiating the measurement light divided by the branching optical element onto the tissue, the multiplexing optical element combining the measurement light reflected by the tissue and the reference light divided by the branching optical element and cause the measurement light and the reference light to interfere with each other, the photodetector detecting an interference signal by receiving interference light generated by the multiplexing optical element, the three-dimensional OCT data being three-dimensional OCT data obtained by irradiating the measurement light on a two-dimensional measurement region, the two-dimensional measurement region extending in a direction intersecting an optical axis of the measurement light; setting a line pattern, from among a plurality of types of line pattern, with respect to the two-dimensional measurement region for which the three-dimensional OCT data is obtained, at least one of an arrangement, a number, or a shape of one or more lines being different for the plurality of types of line pattern; and extracting, from the three-dimensional OCT data, a two-dimensional tomographic image of a cross section intersecting each of the one or more lines of the set line pattern.

DETAILED DESCRIPTION

Figure 1:
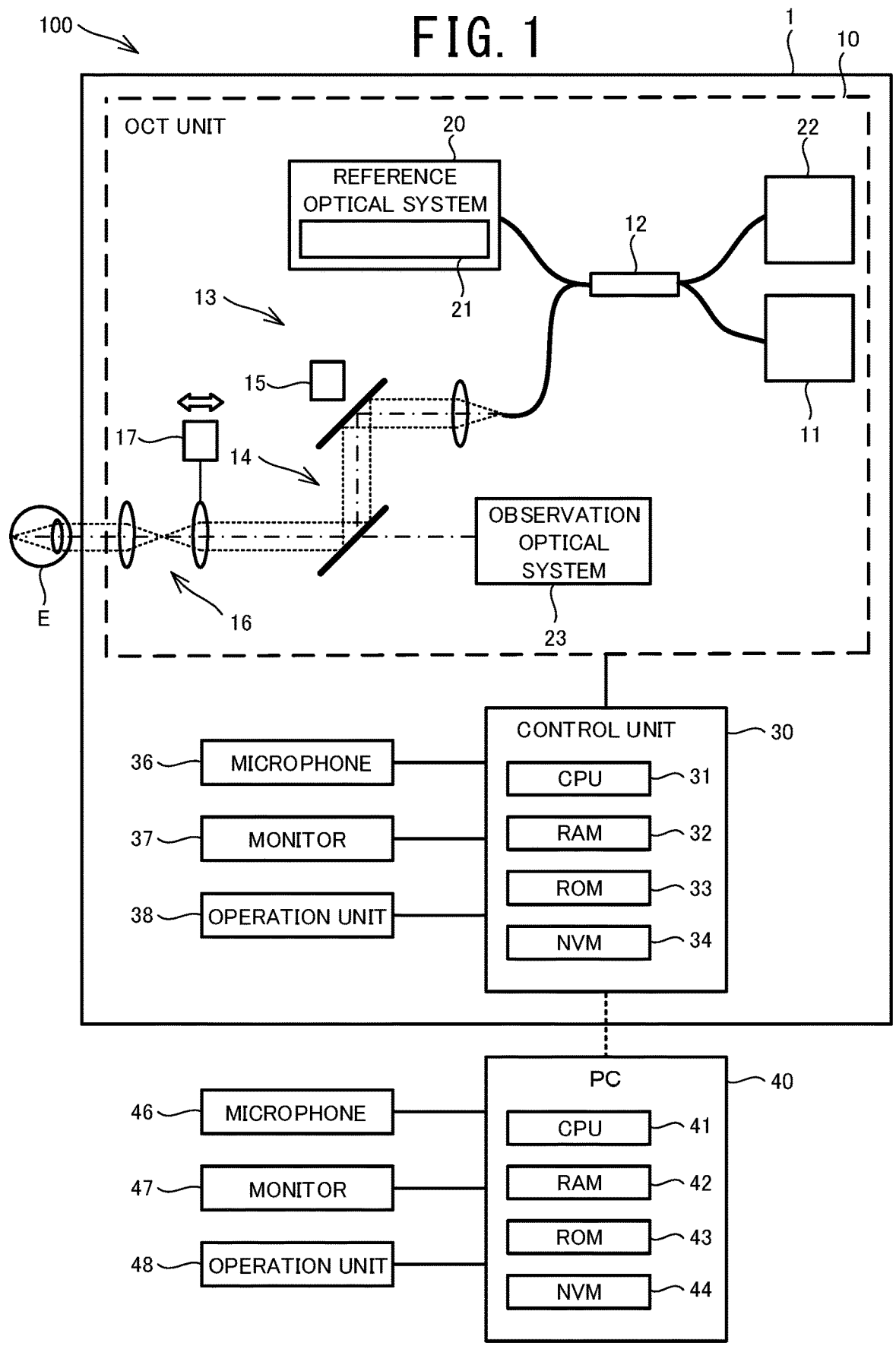
FIG. 1 is a block diagram showing an overall configuration of an OCT system 100.

An OCT data processing device exemplified in the present disclosure processes OCT data of a tissue of a subject's eye acquired by an OCT device. The OCT device includes an OCT light source, a branching optical element, an irradiation optical system, a multiplexing optical element, and a photodetector. The OCT light source emits light (OCT light).

The branching optical element divides the light emitted from the OCT light source into measurement light and reference light. The irradiation optical system irradiates the measurement light divided by the branching optical element onto the tissue. The multiplexing optical element combines the measurement light reflected by the tissue and the reference light divided by the branching optical element and causes the measurement light and the reference light to interfere with each other. The photodetector detects an interference signal by receiving interference light generated by the multiplexing optical element. A processor of the OCT data processing device acquires three-dimensional OCT data obtained by the OCT device. The three-dimensional OCT data is three-dimensional OCT data obtained by irradiating the measurement light on a two-dimensional measurement region extending in a direction intersecting an optical axis of the measurement light. The processor further sets a line pattern, from among a plurality of types of line pattern, with respect to the two-dimensional measurement region for which the three-dimensional OCT data is obtained. At least one of an arrangement, a number, or a shape of one or more lines is different for the plurality of types of line pattern. The processor further extracts, from the three-dimensional OCT data, a two-dimensional tomographic image of a cross section intersecting each of the one or more lines of the set line pattern.

According to the OCT data processing device according to the present disclosure, the two-dimensional tomographic image is extracted from the three-dimensional OCT data acquired by the OCT device, in accordance with a line pattern set from among the plurality of line patterns. Thus, when the OCT data of the test subject is acquired by the OCT device, a photography method executed by the OCT device need not necessarily be set from among a plurality of photography methods. Further, after the three-dimensional OCT data of the test subject is acquired, a user can verify an extraction result of the two-dimensional tomographic image in accordance with various line patterns, without once more performing the photography using the OCT device. Thus, according to the OCT data processing device according to the present disclosure, information relating to the tissue of the test subject can be appropriately acquired.

The processor may further perform processing on data of the extracted two-dimensional tomographic image. For example, the processor may cause the extracted two-dimensional tomographic image to be displayed on a display. The processor may perform analysis processing on the extracted two-dimensional tomographic image (processing to analyze a thickness of a specific layer, for example), and may generate data of an analysis result. The processor may cause the data of the extracted two-dimensional tomographic image to be stored in a memory.

When performing the analysis processing on the two-dimensional tomographic image, the processor may change an analysis method in accordance with the set line pattern. For example, when the line pattern formed of a single straight line is set, the processor may generate data of a graph indicating a thickness of a specific layer on the line. When the line pattern formed of a circular line is set, the processor may calculate an average value of thicknesses of a specific layer of the whole of the circular line. When the line pattern formed of the circular line is set, and when the circular line is divided into a plurality of sections, the processor may calculate an average value of a thicknesses of a specific layer of each of the divided sections. When the circular line is divided into the plurality of sections, for example, there may be a case in which the circle is divided into two sections above and below a center of the circle, a case in which the circular line is divided into four sections, on the side of an ear, an upper side, the side of the nose, and a lower side, or the like.

Various devices may function as the OCT data processing device. For example, the OCT device itself may function as the OCT data processing device of the present disclosure. A device (a personal computer, for example) that is capable of exchanging data with the OCT device may function as the OCT data processing device. A plurality of processors may perform processing in concert with each other.

The OCT device may further include a scanning unit. A scanning unit may cause the measurement light irradiated onto the tissue by the irradiation optical system to scan in a two-dimensional direction intersecting the optical axis. The three-dimensional OCT data may be obtained by a spot of the measurement light being caused by the scanning unit to scan in the two-dimensional measurement region. In this case, the three-dimensional OCT data can be appropriately acquired by the OCT device.

The configuration of the OCT device may be changed. For example, the irradiation optical system of the OCT device may simultaneously irradiate the measurement light onto a two-dimensional region on the tissue of the test subject. In this case, the photodetector may be a two-dimensional photodetector that detects an interference signal in the two-dimensional region on the tissue. Specifically, the OCT device may acquire the OCT data using the principle of so-called full field OCT (FF-OCT). The OCT device may simultaneously irradiate the measurement light onto an irradiation line that extends in a one-dimensional direction on the tissue, and cause the measurement light to scan in a direction intersecting the irradiation line. In this case, the photodetector may be a one-dimensional photodetector (a line sensor, for example) or a two-dimensional photodetector. Specifically, the OCT device may acquire the OCT data using the principle of so-called line field OCT (LF-OCT).

When processing the OCT data newly obtained from the subject's eye for which the OCT data has been obtained in the past, the processor may set the same line pattern, with respect to the measurement region, as a line pattern set when processing the OCT data obtained in the past. In this case, the two-dimensional tomographic image can be extracted using the same pattern as in the past. Thus, a follow-up observation of the subject's eye or the like can be more appropriately performed, for example.

When processing the OCT data newly obtained from the subject's eye for which the OCT data has been obtained in the past, the processor may set the line pattern in the same position as a position at which a line pattern was set when processing the OCT data obtained in the past. In this case, the two-dimensional tomographic image of the same section as in the past can be extracted. Thus, a follow-up observation of the subject's eye or the like can be more appropriately performed, for example.

A method of setting the type and the position of the line pattern may be changed. For example, at least one of the type or the position of the line pattern may be set each time the OCT data is processed, in accordance with an operation command from the user or the like.

The processor may determine a position at which the line pattern is set, based on a result of analysis processing performed on at least one of a two-dimensional front image of the measurement region or the three-dimensional OCT data obtained from the measurement region. In this case, the position at which the line pattern is set can be automatically determined on the basis of a result of the analysis processing. Thus, the OCT data can be more appropriately processed.

Various images may be adopted as the two-dimensional front image that is a target of the analysis processing. For example, the two-dimensional front image may be an image photographed using a principle different from that of OCT (such as a front image photographed by a scanning laser ophthalmoscope, a front image photographed by a fundus camera, a front image photographed by an infra-red camera, or the like, for example). The two-dimensional front image may be a front image acquired from the three-dimensional OCT data (such as an integrated image integrated in relation to a depth direction, a front image at each of XY positions at a given depth in a depth direction, a front image of a surface layer of the tissue, or the like, for example). The two-dimensional front image and the three-dimensional OCT data may be obtained by different devices.

A specific method for determining the position at which to set the line pattern on the basis of the result of the analysis processing may be selected as appropriate. For example, the processor may extract a feature section that is present in the measurement region, by performing image processing, which is a type of the analysis processing, on the two-dimensional front image. For example, when the measurement region is the ocular fundus of the subject's eye, the feature section may be at least one of an optic papilla, a macula lutea, a blood vessel, a lesion, or the like. The processor may set the line pattern with respect to the measurement region on the basis of a positional relationship between the extracted feature section and the line pattern to be set. The processor may determine the position of the line pattern by matching positional relationships between a plurality of two-dimensional front images, using image processing. The processor may perform analysis processing on the three-dimensional OCT image and may extract, as the feature section, an uneven section, a section having a color that is different to its surroundings, or the like. The processor may automatically determine the position at which to set the line pattern on the basis of other information (such as various medical information, for example).

The processor may determine the position at which to set the line pattern without using the result of the analysis processing. For example, the processor may set the line pattern at a position specified by an operation command, when the user inputs the operation command (a command operation using a touch panel, a mouse, or the like, for example) in a state in which the two-dimensional front image is displayed on the display.

The processor may create a line pattern in accordance with an operation command input from a user. The processor may cause information of the created line pattern to be stored in a memory as one of the plurality of types of line pattern. In this case, the user can create, as one of the plurality of types of line pattern, an appropriate line pattern that the user desires. As a result, the three-dimensional OCT data can be more appropriately processed.

The processor of the OCT device may automatically acquire the three-dimensional OCT data when a trigger signal is generated that starts the acquisition of the OCT data of the tissue. In this case, the user can appropriately verify extraction results of various two-dimensional tomographic images obtained by processing the three-dimensional OCT data, even without specifying a scan pattern of the measurement light. A method for generating the trigger signal may be selected as appropriate. For example, the trigger signal may be generated when an operation command is received from the user to cause the acquisition of the OCT data (namely, the photographing) to be started. The trigger signal may be automatically generated when photography preparation (alignment of the OCT device with respect to the subject's eye, adjustment of the optical path length, adjustment of the focus, and the like, for example) are complete.

This OCT device may be realized as follows. An OCT device acquiring OCT data of a tissue by processing interference light caused by reference light and reflected light of measurement light irradiated onto the tissue of a subject's eye, the OCT device including: an OCT light source; a branching optical element dividing light emitted from the OCT light source into the measurement light and the reference light; an irradiation optical system irradiating the measurement light divided by the branching optical element onto the tissue; a scanning unit causing the measurement light irradiated onto the tissue by the irradiation optical system to scan in a two-dimensional direction intersecting an optical axis of the measurement light; a multiplexing optical element combining the measurement light reflected by the tissue and the reference light divided by the branching optical element and causing the measurement light and the reference light to interfere with each other; a photodetector detecting an interference signal by receiving interference light generated by the multiplexing optical element; and a processor performing control of the OCT device, the processor acquiring the OCT data being three-dimensional, by causing, when a trigger signal to start acquisition of the OCT data is generated, the measurement light to scan in a two-dimensional measurement region, the two-dimensional measurement region extending in a direction intersecting the optical axis of the measurement light.

The processor may acquire the three-dimensional OCT data each time the trigger signal is generated, in a state in which processing to receive a selection command of a pattern (scan pattern) used for the measurement light to scan is omitted. The processor may set one of a plurality of types of line pattern after acquiring the three-dimensional OCT data, and may extract the two-dimensional tomographic image in accordance with the set line pattern. As a result, the two-dimensional tomographic image can be appropriately obtained even without the user specifying the scan pattern.

A configuration may be adopted in which a plurality of modes are provided, including a mode to determine the scan pattern in accordance with a selection command from the user, and an automatic mode to automatically acquire the three-dimensional OCT data when the trigger signal is generated. When the automatic mode is selected, the processor may automatically acquire the three-dimensional OCT data in accordance with the generation of the trigger signal.

Hereinafter, an exemplary embodiment of the present disclosure will be described. For example, an OCT system 100 of the present embodiment can acquire and process OCT data of an ocular fundus tissue, when a test subject is the ocular fundus of a subject's eye E. However, at least a part of the technology exemplified in the present disclosure may be applied when processing OCT data of a tissue other than that of the ocular fundus in the subject's eye E (such as an anterior ocular segment of the subject's eye E, for example), or OCT data of a test subject other than the subject's eye E (such as skin, a digestive organ, the brain, or the like, for example). The OCT data is data acquired on the basis of the principle of optical coherence tomography (OCT).

An overall configuration of the OCT system 100 of the present embodiment will be described with reference to FIG.

1. The OCT system 100 of the present embodiment includes an OCT device 1 and a personal computer (hereinafter referred to as a "PC") 40. The OCT device 1 acquires OCT data of the subject's eye E. The PC 40 performs processing of the OCT data acquired by the OCT device 1 (such as processing to extract a two-dimensional tomographic image from the three-dimensional OCT data, for example).

The OCT device 1 includes an OCT unit 10 and a control unit 30. The OCT unit 10 includes an OCT light source 11, a coupler (optical splitter) 12, a measurement optical system 13, a reference optical system 20, a photodetector 22, and a front observation optical system 23.

The OCT light source 11 emits light (OCT light) for acquiring the OCT data. The coupler 12 splits the OCT light emitted from the OCT light source 11 into measurement light and reference light. Further, the coupler 12 of the present embodiment combines measurement light reflected by the test subject (the ocular fundus of the subject's eye E in the present embodiment), and reference light generated by the reference optical system 20, and causes the reflected measurement light and the reference light to interfere with each other. In other words, the coupler 12 of the present embodiment functions both as a branching optical element that divides the OCT light into the measurement light and the reference light, and as a multiplexing optical element that combines the reflected light of the measurement light and the reference light. The configuration of at least one of the branching optical element and the multiplexing optical element may be changed. For example, an element other than the coupler (a circulator, a beam splitter, or the like, for example) may be adopted.

As well as guiding the measurement light divided by the coupler 12 to the test subject, the measurement optical system 13 returns the measurement light reflected by the test subject to the coupler 12. The measurement optical system 13 includes a scanning unit 14, an irradiation optical system 16, and a focus adjustment unit 17. As a result of being driven by a drive unit 15, the scanning unit 14 can cause the measurement light to scan (deflect) in a two-dimensional direction that intersects an optical axis of the measurement light. In the present embodiment, two galvanometer mirrors that can deflect the measurement light in mutually different directions are used as the scanning unit 14. However, another device that deflects the light (at least one of a polygon mirror, a resonant scanner, an acousto-optic device, or the like, for example) may be used as the scanning unit 14. The irradiation optical system 16 is provided further to a downstream side (namely, to the side of the test subject), of an optical path, than the scanning unit 14. The irradiation optical system 16 irradiates the measurement light onto a tissue of the test subject. The focus adjustment unit 17 adjusts a focus of the measurement light by moving an optical member (a lens, for example) of the irradiation optical system 16 in a direction along the optical axis of the measurement light.

The reference optical system 20 generates the reference light and returns the reference light to the coupler 12. The reference optical system 20 of the present embodiment generates the reference light by causing the reference light divided by the coupler 12 to be reflected by a reflection optical system (a reference mirror, for example). However, the configuration of the reference optical system 20 may be changed. For example, the reference optical system 20 may cause the light incident from the coupler 12 to pass through without being reflected and return the light to the coupler 12. The reference optical system 20 includes an optical path length difference adjustment unit 21 that changes the optical path length difference between the measurement light and the reference light. In the present embodiment, the optical path length difference is changed by moving the reference mirror in the optical axis direction. The configuration for changing the optical path length difference may be provided in an optical path of the measurement optical system 13.

The photodetector 22 detects an interference signal by receiving interference light of the measurement light and the reference light generated by the coupler 12. In the present embodiment, the Fourier domain OCT principle is adopted. In Fourier domain OCT, a spectral intensity of the interference light (a spectral interference signal) is detected by the photodetector 22 and a complex OCT signal is acquired using a Fourier transform on data of the spectral intensity. Spectral-domain-OCT (SD-OCT), swept-source-OCT (SS-OCT), and the like may be used as examples of the Fourier domain OCT. For example, time-domain-OCT (TD-OCT) and the like may also be adopted.

In the present embodiment, SD-OCT is adopted. In the case of SD-OCT, for example, as well as a low coherent light source (broadband light source) being used as the OCT light source 11, a spectro-optical system (a spectrometer), which divides the interference light into frequency components (wavelength components) is provided in the vicinity of the photodetector 22 on the optical path of the interference light. In the case of SS-OCT, for example, a wavelength scanning light source (wavelength tunable light source) that changes an emitted wavelength at high speed temporally is used as the OCT light source 11. In this case, the OCT light source 11 may include a light source, a fiber ring resonator, and a wavelength selecting filter. For example, the wavelength selecting filter may be a filter using a diffraction grating and a polygon mirror in combination, a filter using a Fabry-Perot etalon structure, and the like.

In the present embodiment, a three-dimensional OCT data is acquired by a spot of the measurement light being scanned in a two-dimensional measurement region by the scanning unit 14. However, the principle by which the three-dimensional OCT data is acquired may be changed. For example, the three-dimensional OCT data may be acquired using the principle of line field OCT (hereinafter referred to as "LF-OCT"). In LF-OCT, the measurement light is simultaneously irradiated onto an irradiation line that extends in a one-dimensional direction in a tissue, and the interference light between the reflected light of the measurement light and the reference light is received by a one-dimensional photodetector (a line sensor, for example) or a two-dimensional photodetector. By causing the measurement light to scan in a direction that intersects the irradiation line, in the two-dimensional measurement region, the three-dimensional OCT data is acquired. The three-dimensional OCT data may be acquired using the principle of full field OCT (hereinafter referred to as "FF-OCT"). In FF-OCT, as well as the measurement light being irradiated onto the two-dimensional measurement region on a tissue, the interference light between the reflected light of the measurement light and the reference light is received by a two-dimensional photodetector. In this case, the OCT device 1 need not necessarily include the scanning unit 14.

The front observation optical system 23 is provided to acquire a two-dimensional front image of a tissue of the test subject (the ocular fundus of the subject's eye E in the present embodiment). The two-dimensional front image in the present embodiment is a two-dimensional image when the tissue is seen from a direction (the front direction) along the optical axis of the OCT measurement light. For the configuration of the front observation optical system 23, for example, a configuration can be adopted using at least one of a scanning laser ophthalmoscope (SLO), a fundus camera, an infra-red camera that photographs a front image by batch irradiating infra-red light onto a two-dimensional image photograph range, or the like.

The OCT device 1 may acquire a three-dimensional OCT data of the tissue, and may acquire, as the two-dimensional front image, an image when the tissue is seen from the direction (the front direction) along the optical axis of the measurement light (a so-called "Enface image"). Data of the Enface image may be, for example, integrated image data in which luminance values are integrated in a depth direction (a Z direction) at each position in an XY direction, integrated values of spectral data at each position in the XY direction, luminance data at each position in the XY direction at a given depth in a depth direction, luminance data at each of positions in the XY direction at a layer of the retina (the surface layer of the retina, for example), or the like. When the Enface image is acquired, the front observation optical system 23 may be omitted.

The control unit 30 performs various controls of the OCT device 1. The control unit 30 include a CPU 31, a RAM 32, a ROM 33, and a non-volatile memory (NVM) 34. The CPU 31 is a controller that performs various controls. The RAM 32 temporarily stores various information. The ROM 33 stores programs executed by the CPU 31, various default values, and the like. The NVM 34 is a non-transitory storage medium that can hold storage content even if a power supply is cut off. The NVM 34 may store an OCT data acquisition program used to perform OCT data acquisition processing (to be described below, refer to FIG. 2).

A microphone 36, a monitor 37, and an operation unit 38 are connected to the control unit 30. The microphone 36 inputs sound. The monitor 37 is an example of a display that displays various images. The operation unit 38 is operated by the user to input various operation commands to the OCT device 1. Various devices may be used as the operation unit 38, for example, such as a mouse, a keyboard, a touch panel, or a foot switch. The various operation commands may be input to the OCT device 1 by inputting sound to the microphone 36. In this case, the CPU 31 may determine the type of an operating instruction by performing audio recognition processing with respect to the input sound.

In the present embodiment, the integrated OCT device 1 is exemplified in which the OCT unit 10 and the control unit 30 are housed in a single housing. However, the OCT device 1 may include a plurality of devices having different housings. For example, the OCT device 1 may include an optical device in which the OCT unit 10 is mounted, and a PC connected by a wired connection or wirelessly to the optical device. In this case, a control unit of the optical device and a control unit of the PC may function as the control unit 30 of the OCT device 1.

An overall configuration of the PC 40 will be described. The PC 40 includes a CPU 41, a RAM 42, a ROM 43, and an NVM 44. The NVM 44 may store an OCT data processing program, which is used to perform OCT data processing (to be described below, refer to FIG. 4). A microphone 46, a monitor 47, and an operation unit 48 are connected to the PC 40. The microphone 46 inputs sound. The monitor 47 is an example of a display that displays various images. The operation unit 48 is operated by the user to input various operation commands to the PC 40. Similarly to the operation unit 38 of the OCT device 1, various devices may be used as the operation unit 48, for example, such as a mouse, a keyboard, or a touch panel. The various operation commands may be input to the PC 40 by inputting sound to the microphone 46.

The PC 40 can acquire various pieces of data from the OCT device 1 (the three-dimensional OCT data obtained by the OCT device 1, for example). The various pieces of data may be acquired, for example, by at least one of wired communication, wireless communication, a removable storage device (a USB memory, for example), or the like.

OCT Data Acquisition Processing

Figure 2:
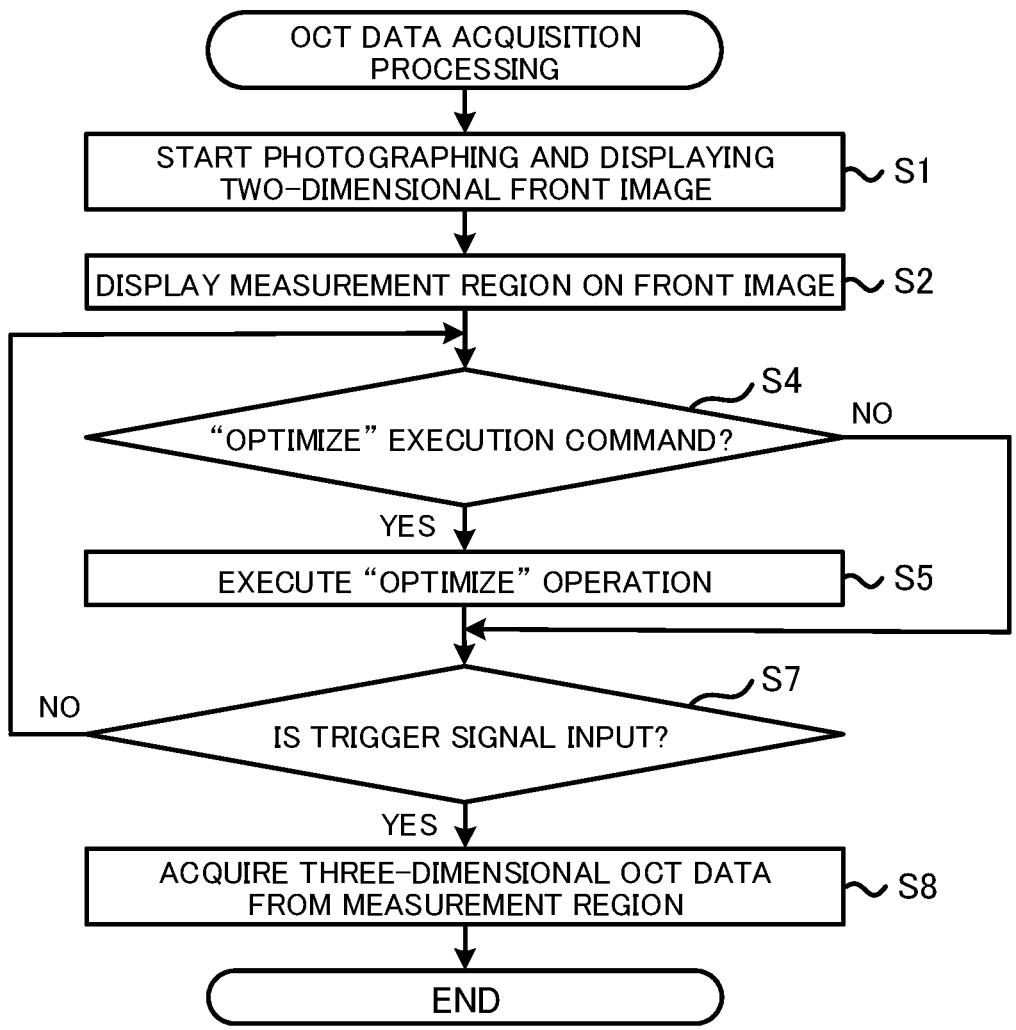
FIG. 2 is a flowchart showing an example of OCT data acquisition processing.

The OCT data acquisition processing performed by the OCT device 1 will be described with reference to FIG. 2 and FIG. 3. The CPU 31 of the OCT device 1 performs the OCT data acquisition processing shown in FIG. 2, in accordance with the OCT data acquisition program stored in the NVM 34.

An automatic mode, and a mode in which a scan pattern is selected by the user are provided in the OCT device 1 of the present embodiment. The automatic mode is a mode in which the three-dimensional OCT data is automatically acquired when a trigger signal is generated to start acquiring the OCT data. The scan pattern is a pattern for scanning the measurement light. The processing illustrated in FIG. 2 is executed when the automatic mode is selected. According to the processing illustrated in FIG. 2, the user can obtain a processing result of an appropriate three-dimensional OCT data, without selecting the scan pattern.

First, the CPU 31 starts capturing a two-dimensional front image of a tissue (the ocular fundus of the subject's eye E in the present embodiment), which is a target of the OCT data acquisition, and causes the photographed image to be displayed on the monitor 37 (S1). FIG. 3 shows an example of a two-dimensional front image 50 displayed on the monitor 37. In the example shown in FIG. 3, inside the two-dimensional front image 50, an optic papilla (hereinafter also sometimes referred to as a "papilla") 51, a macula lutea 52, and ocular fundus blood vessels 53 of the subject's eye E are pictured. The two-dimensional front image 50 is intermittently and repeatedly photographed and is displayed as a moving image on the monitor 37.

Next, the CPU 31 causes a measurement region 55 to be displayed on the two-dimensional front image 50 (S2). The measurement region 55 is a region, of the tissue, that is a target of acquiring the OCT data. The measurement region 55 is a two-dimensional region extending in a direction that intersects the optical axis of the measurement light. When an operation to acquire the OCT data (namely, a photographing operation) is started, the measurement light is irradiated within the measurement region 55.

Figure 3:
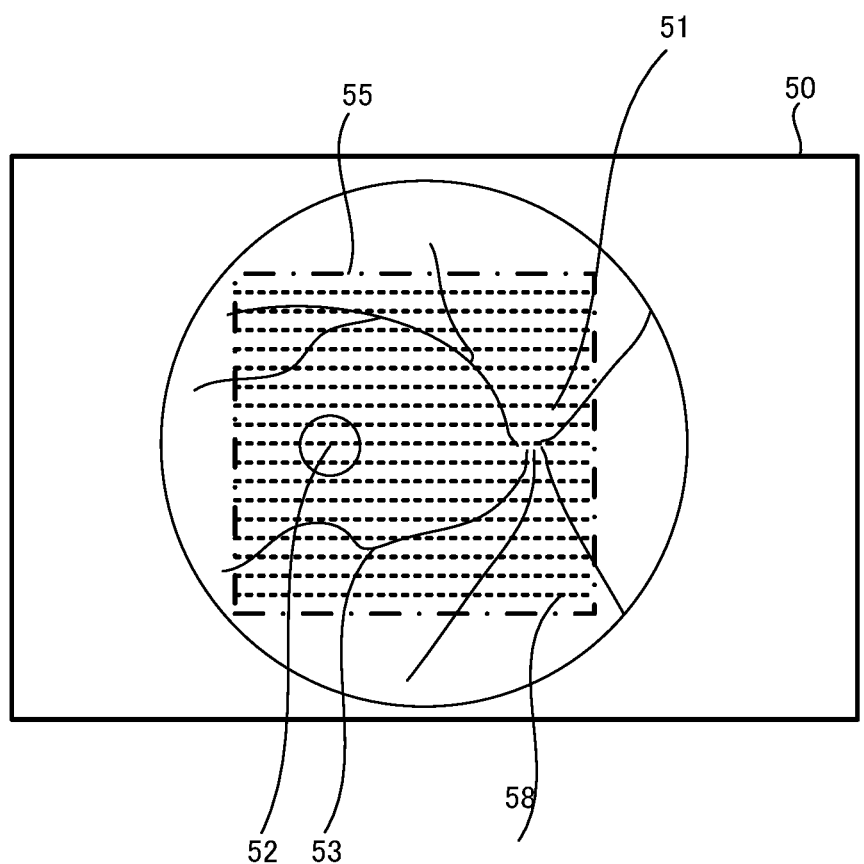
FIG. 3 is a diagram showing an example of a two-dimensional front image 50.

In the example shown in FIG. 3, a frame portion of the measurement region 55 is electronically displayed on the two-dimensional front image 50. However, a display method of the measurement region 55 may be changed as appropriate. For example, light indicating the frame portion of the measurement region 55 may be directly irradiated onto the tissue. In this case, the user can ascertain the measurement region 55 by verifying a position of the light captured in the two-dimensional front image 50. In the example shown in FIG. 3, the measurement region 55 is rectangular. However, the measurement region 55 may be a shape other than the rectangular shape (a circular shape or the like, for example).

The user aligns the OCT device 1 with respect to the test subject while verifying the two-dimensional front image 50, and performs adjustment such that the measurement region 55 is in an appropriate position with respect to the tissue. In the present embodiment, since the papilla 51 and the macula lutea 52 are both included in the measurement region 55, the adjustment is performed such that a center of the measurement region 55 is positioned between the papilla 51 and the macula lutea 52. In this case, in the OCT data processing to be described below (refer to FIG. 4), a two-dimensional tomographic image of both the papilla 51 and the macula lutea 52 can be extracted. The alignment of the OCT device 1 with respect to the test subject may be automatically performed.

Next, the CPU 31 determines whether an "Optimize" command is input (S4). "Optimize" is a function to adjust the optical path length difference using the optical path length adjustment unit 21 (refer to FIG. 1) and optimize the focus using the focus adjustment unit 17. When the "Optimize" execution command is input (yes at S4), the CPU 31 performs the "Optimize" operation (S5), and advances the processing to S7. When the "Optimize" command is not input (no at S4), the processing advances straight to S7.

Next, the CPU 31 determines whether the trigger signal to start the acquisition of the OCT data is generated (is input, in the present embodiment) (S7). For example, in the present embodiment, the trigger signal is generated and input to the CPU 31 by the user operating a "Release" button (not shown in the drawings) to instruct the start of acquisition of the OCT data, in a state in which the alignment and the "Optimize" operation are complete. However, the method of generating the trigger signal may be changed. For example, the trigger signal may be generated by a specific audio being input into the microphone 36. At a point in time at which photography preparation (the alignment and the "Optimize" operation, for example) is complete, the CPU 31 may automatically generate the trigger signal, and may automatically start the acquisition of the OCT data. When the trigger signal is not generated (no at S7), the processing returns to S4.

When the trigger signal is generated (yes at S7), the CPU 31 performs processing to acquire the three-dimensional OCT data from the measurement region 55 of the tissue (S8). The CPU 31 of the present embodiment controls the scanning unit 14, and causes the spot of the measurement light to scan in the two-dimensional measurement region 55, and thus acquires the three-dimensional OCT data of the measurement region 55. For example, in the present embodiment, as shown in FIG. 3, a plurality of straight scanning lines (scan lines) 58 along which the spot is caused to scan are set at equal intervals inside the measurement region 55, and the spot of the measurement light is caused to scan each of the scanning lines 58, and thus the three-dimensional OCT data of the measurement region 55 is acquired.

As described above, in the present embodiment, when the trigger signal to start the acquisition of the OCT data is generated, the three-dimensional OCT data of the measurement region 55 is automatically acquired. Thus, even without specifying the photography method, the user can appropriately verify extraction results of the various two-dimensional tomographic images obtained by processing the three-dimensional OCT data.

OCT Data Processing

Figure 4:
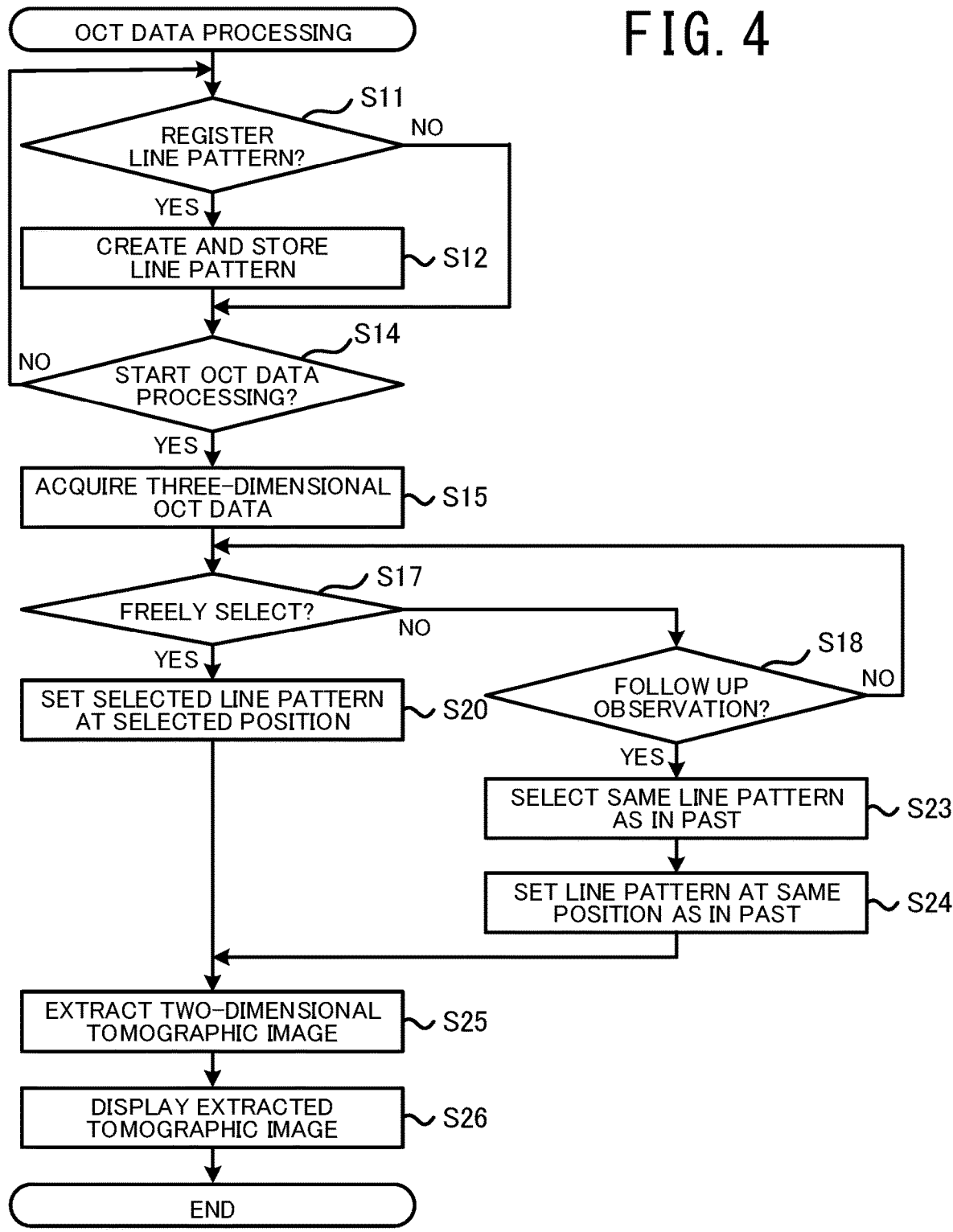
FIG. 4 is a flowchart showing an example of OCT data processing.
Figure 5:
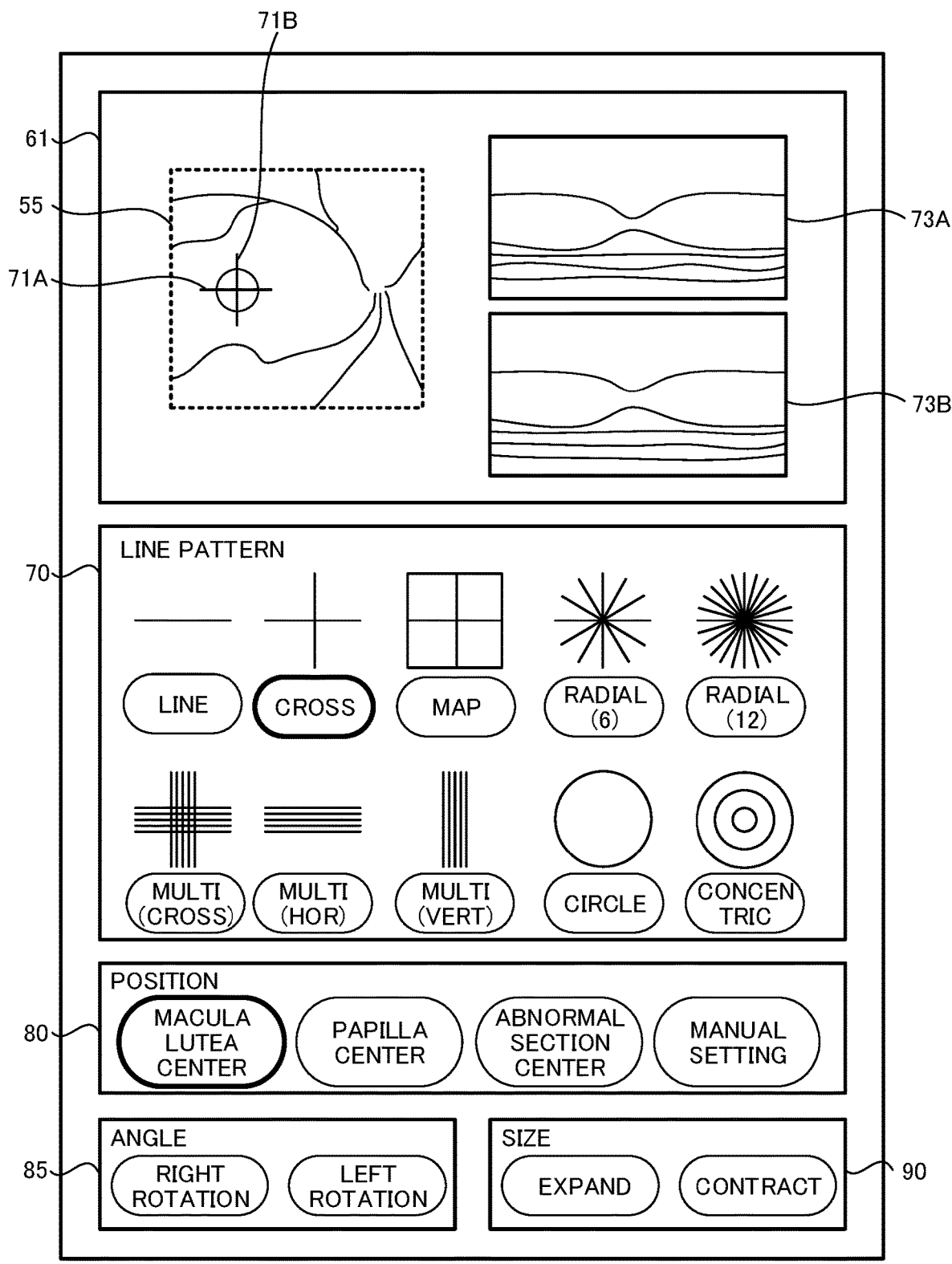
FIG. 5 is a diagram showing an example of an image displayed on a monitor 47 when a user selects a line pattern.

The OCT data processing will be described with reference to FIG. 4 and FIG. 5. In the OCT data processing, by processing the three-dimensional OCT data obtained by the OCT data acquisition processing (refer to FIG. 2), an appropriate two-dimensional tomographic image is extracted. In the present embodiment, the PC 40 acquires the three-dimensional OCT data from the OCT device 1, and extracts the two-dimensional tomographic image. In other words, in the present embodiment, the PC 40 functions as an OCT data processing device. However, another device may function as the OCT data processing device. For example, the OCT device 1 itself may perform the OCT data processing. A plurality of processors (the CPU 31 of the OCT device 1, and the CPU 41 of the PC 40, for example) may perform the OCT data processing in concert with each other. In the present embodiment, the CPU 41 of the PC 40 performs the OCT data processing shown in FIG. 4, in accordance with the OCT data processing program stored in the NVM 44.

First, the CPU 41 determines whether an operation command is input to newly register a line pattern (S11). Examples of a plurality of types of line pattern are shown in a line pattern selection field 70 of an option selection screen shown in FIG. 5. Each of the line patterns includes one or more lines. The line included in the line patterns indicates a position at which the two-dimensional tomographic image is extracted from the three-dimensional OCT data. Specifically, when a line pattern is set with respect to the measurement region 55, a two-dimensional tomographic image of a cross section intersecting the line of the set line pattern is extracted. For example, in the present embodiment, a two-dimensional tomographic image of a cross section perpendicularly intersecting the two-dimensional measurement region 55 is extracted.

When the operation command to newly register the line pattern is input (yes at S11), the CPU 41 creates the new line pattern in accordance with the operation command input from the user. The CPU 41 causes information of the created line pattern to be stored in a memory (the NVM 44 in the present embodiment), as one of the plurality of types of line pattern (S12). The CPU 41 can newly create various line patterns. For example, the CPU 41 may create, as the new line pattern, a line pattern created by combining a plurality of the line patterns displayed in the line pattern selection filed 70 shown in FIG. 5.

Next, the CPU 41 determines whether a command to start processing of the three-dimensional OCT data is input (S14). When the command is not input (no at S14), the processing returns to S11. When the start command is input (yes at S14), the CPU 41 acquires the three-dimensional OCT data obtained from the target test subject by the OCT device 1 (S15). The three-dimensional OCT data may be acquired via at least one of wired communication, wireless communication, a network, a removable memory, or the like.

It is sufficient that the three-dimensional OCT data includes three-dimensional data of the tissue of the test subject. For example, the OCT device 1 may generate motion contrast data by processing a plurality of pieces of OCT data that relate to the same position of the tissue of the test subject but are captured at different timings. The motion contrast data indicates movement in the tissue. There may be a case in which the three-dimensional data of the tissue is not included in the generated motion contrast data itself. However, information in the depth direction is included in the OCT data acquired to generate the motion contrast data. Thus, the three-dimensional OCT data acquired to generate the motion contrast data of the two-dimensional measurement region 55 may be acquired by the CPU 41 separately from the motion contrast data, or together with the motion contrast data.

Next, processing is performed (S17 to S26) to set the line pattern and extract the two-dimensional tomographic image. In the present embodiment, by inputting an operation command, the user can specify one of processing to freely select and set a line pattern, and processing to appropriately perform a follow-up observation with respect to the same test subject.

When "freely select" is specified (yes at S17), the CPU 41 sets the line pattern selected by the user at the selected position with respect to the measurement region 55 (S20). The CPU 41 extracts, from the three-dimensional OCT data, a two-dimensional tomographic image of a cross section that intersects each of one or more lines of the set line pattern (S25). The CPU 41 causes the extracted two-dimensional tomographic image to be displayed on the monitor 47.

An example of the processing when the user selects a desired line pattern will be described with reference to FIG. 5. In the present embodiment, when "freely select" is specified, the option selection screen exemplified in FIG. 5 is displayed on the monitor 47. A processing result display field 61, the line pattern selection field 70, a position specification field 80, an angle specification filed 85, and a size specification field 90 are formed in the option selection screen.

The plurality of types of line pattern, for which at least one of an arrangement, a number, or a shape of one or more lines are mutually different, are displayed in the line pattern selection field 70. The user can freely select one or more line patterns, from among the plurality of types of line pattern. In the example shown in FIG. 5, a "cross" line pattern is selected, by inputting an operation command to specify a button of the "cross" in which two lines perpendicularly intersect each other.

A position on the measurement region 55 at which the selected line pattern is to be set is specified in the position specification field 80. For example, "macula lutea center," "papilla center," "abnormal section center," and "manual setting" buttons are provided in the position specification field 80 of the present embodiment. When the "macula lutea center" is specified, the position of the selected line pattern is set such that the center of the line pattern is aligned with the macula lutea. When the "papilla center" is specified, the position of the selected line pattern is set such that the center of the line pattern is aligned with the papilla. When the "abnormal section center" is specified, the position of the selected line pattern is set such that the center of the line pattern is aligned with an abnormal section in the tissue. When the "manual setting" is specified, the position of the line pattern is set at a position on the measurement region 55 specified by an operation command of the user. A method for the user to specify the position in the "manual setting" may be selected as appropriate. For example, the user may specify a center position of the line pattern by performing a click operation when a cursor has been moved to a desired position by operating the mouse.

In the present embodiment, the CPU 41 can perform analysis processing on at least one of the two-dimensional front image of the measurement region 55 or the three-dimensional OCT data, and can determine the position at which to set the line pattern on the basis of a result of the analysis processing. For example, in the present embodiment, the CPU 41 detects the position of the papilla 51 and the position of the macula lutea 52, by performing image processing on the two-dimensional front image of the measurement region 55. When the abnormal section is present in the measurement region 55, the CPU 41 can detect the position of the abnormal section using the image processing. When one of the "macula lutea center," the "papilla center," or the "abnormal section center" is specified, the CPU 41 aligns the center of the selected line pattern with the position detected by the image processing. However, the position of the line pattern may be determined without using the image processing. For example, the CPU 41 may analyze the three-dimensional OCT data obtained from the measurement region 55, may extract a feature section (at least one of the macula lutea, the papilla, or the abnormal section, for example), and may determine the position of the line pattern on the basis of an extraction result. The CPU 41 may prompt the user to operate the operation unit and cause the user to specify the position of the feature section on the measurement region 55.

An angle used when setting the selected line pattern on the measurement region 55 is specified in the angle specification field 85. For example, "right rotation" and "left rotation" buttons are provided in the angle specification field 85 of the present embodiment. When the buttons are operated, the selected line pattern is rotated on the measurement region 55 in accordance with the operated button. A size of the selected line pattern on the measurement region 55 is specified in the size specification field 90. "Expand" and "contract" buttons are provided in the size specification field 90 of the present embodiment. When the button is operated, the size of the selected line pattern on the measurement region 55 is changed in accordance with the operated button.

The two-dimensional front image of the measurement region 55 on which the line pattern is set, and the two-dimensional tomographic image extracted in accordance with the set line pattern are displayed in the processing result display field 61. In the example shown in FIG. 5, the "cross" is selected as the line pattern, and the "macula lutea center" is selected as the position of the line pattern. Thus, the CPU 41 causes a horizontal direction line 71A and a line 71B in a perpendicular direction to the line 71A that are included in the "cross" line pattern to be displayed on the two-dimensional front image of the measurement region 55 such that the center of the line pattern is aligned with the macula lutea. Further, the CPU 41 extracts a two-dimensional tomographic image 73A and a two-dimensional tomographic image 73B from the three-dimensional OCT data, and causes the two-dimensional tomographic images 73A and 73B to be displayed in the processing result display field 61. The two-dimensional tomographic image 73A is a two-dimensional tomographic image of a cross section intersecting the line 71A. The two-dimensional tomographic image 73B is a two-dimensional tomographic image of a cross section intersecting the line 71B.

The method for setting the line pattern when "free selection" is specified may be changed. For example, a configuration may be adopted in which the type and the position of the line pattern can be simultaneously selected. In this case, for example, when a "macula lutea disease diagnosis" button is operated, as well as selecting the "cross" and "map" line patterns, the CPU 41 may set the positions of the line patterns such that the centers of the selected line patterns are aligned with the macula lutea. When a "papilla disease diagnosis" button is operated, as well as selecting the "circle" and "map" line patterns, the CPU 41 may set the positions of the line patterns such that centers of the selected line patterns are aligned with the papilla. A configuration may be adopted in which the user can register the set line pattern in advance. In this case, the user need not necessarily perform the operation to select the line pattern each time.

The CPU 41 may set the line pattern in accordance with an analysis result that the user wishes to verify. For example, when a graph indicating a thickness of a specific layer on a single straight line is selected as the analysis result desired by the user, the CPU 41 may include the "line" shown in FIG. 5 in the line pattern. When a graph of average values of thicknesses of individual sections on a circular line is selected as the analysis result desired by the user, the CPU 41 may include the "circle" in the line pattern.

When "follow up observation" processing is specified (yes at S18), the CPU 41 selects the same line pattern as the line pattern set when processing the OCT data obtained in the past, as the line pattern to be set this time with respect to the measurement region 55 (S23). The CPU 41 sets the line pattern at the same position as the position at which the line pattern was set when processing the OCT data obtained in the past (S24). The CPU 41 extracts a two-dimensional tomographic image of a cross section intersecting the line of the set line pattern, from the three-dimensional OCT data (S25). The CPU 41 causes the extracted two-dimensional tomographic image to be displayed on the monitor 47 (S26).

The "position" at S24 may include the angle and the size of the line pattern. Information about the type and the position of the line pattern set in the past may be acquired by various methods. For example, when the three-dimensional OCT data has been acquired and processed from the tissue of the same test subject in the past, the CPU 41 may acquire data of the processing result and may use information included in the acquired data.

When "follow up observation" processing is specified, the OCT data obtained in the past may be different to the type of the three-dimensional OCT data acquired by the OCT device 1 of the present embodiment. For example, the OCT data obtained in the past may be two-dimensional OCT data obtained using a specific scan pattern by the conventional OCT device. In this case, the CPU 41 determines, as the line pattern to be set this time, the same line pattern as the scan pattern of measurement light executed when the conventional OCT data was obtained. Further, in the measurement region 55, the CPU 41 sets the line pattern to the position scanned by the measurement light when the conventional OCT data was obtained. As a result, even when the type of the OCT data obtained in the past is different to the type of the OCT data to be obtained this time, the follow up observation can be appropriately performed.

In the processing at S24, the image processing is performed on the two-dimensional front image of the measurement region 55, and the position of the line pattern is determined on the basis of a result of the image processing. More specifically, the CPU 41 matches the two-dimensional front image of the measurement region 55 when the line pattern was set in the past with the position of the two-dimensional front image acquired this time, using the image processing. The CPU 41 uses the result of matching the two two-dimensional front images, and sets the line pattern at the same position as the position set in the past. However, a specific method for determining the position of the line pattern may be changed as appropriate. For example, the CPU 41 may detect the position of a feature section of the tissue using the image processing, and may determine the position of the line pattern on the basis of the detected position in a similar manner to the processing at S20 that is explained above.

In the processing at S25, the CPU 41 may adjust the data of the two-dimensional tomographic image to be extracted in accordance with a resolution in the XY direction (the direction intersecting the measurement light) of the two-dimensional tomographic image to be extracted. For example, when simply extracting the two-dimensional tomographic image from the three-dimensional OCT data, when the resolution in the XY direction of the two-dimensional tomographic image to be extracted is not sufficient, the CPU 41 may perform adjustment processing to complement pixel values and increase the resolution. In this case, the insufficient pixel values may be complemented using image processing technology, artificial intelligence (AI) technology and the like, for example. The pixel values to be complemented may be calculated on the basis of pixel values of a plurality of pixels positioned surrounding a position of the pixel value to be complemented. The above processing may be applied when a line of the set line pattern passes through a gap between points (pixels) of the three-dimensional OCT data. When simply extracting a plurality of the two-dimensional tomographic images from one or a plurality of pieces of three-dimensional OCT data, when differences occur between the resolutions in the XY direction of the extracted plurality of two-dimensional tomographic images, the CPU 41 may perform thinning adjustment processing by causing the pixel values of a higher resolution two-dimensional tomographic image to be matched with that of a lower resolution. In this case, since the differences between the resolutions of the plurality of two-dimensional tomographic images become smaller, a diagnosis or the like can be more appropriately performed. The CPU 41 may smooth out roughness in the image by performing image processing on the extracted two-dimensional tomographic image. In this case also, artificial intelligence technology (such as deep learning or the like, for example) may be used.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. An optical coherence tomography (OCT) data processing device for use with a tissue of a subject's eye, the OCT data processing device comprising:
  a processor programmed to:
    acquire three-dimensional OCT data, the three-dimensional OCT data being OCT data of a tissue of a subject's eye acquired by an OCT device, the OCT device comprises an OCT light source, a branching optical element, an irradiation optical system, a multiplexing optical element, and a photodetector, the branching optical element dividing light emitted from the OCT light source into measurement light and reference light, the irradiation optical system irradiating the measurement light divided by the branching optical element onto the tissue, the multiplexing optical element combining the measurement light reflected by the tissue and the reference light divided by the branching optical element and cause the measurement light and the reference light to interfere with each other, the photodetector detecting an interference signal by receiving interference light generated by the multiplexing optical element, the three-dimensional OCT data being three-dimensional OCT data obtained by irradiating the measurement light on a two-dimensional measurement region, the two-dimensional measurement region extending in a direction intersecting an optical axis of the measurement light;
    set a line pattern, from among a plurality of types of line pattern, with respect to the two-dimensional measurement region for which the three-dimensional OCT data is obtained, at least one of an arrangement, a number, or a shape of one or more lines being different for the plurality of types of line pattern; and extract, from the three-dimensional OCT data, a two-dimensional tomographic image of a cross section intersecting each of the one or more lines of the set line pattern.

2. The OCT data processing device according to claim 1, wherein the OCT device further comprises:

a scanning unit configured to cause the measurement light irradiated onto the tissue by the irradiation optical system to scan in a two-dimensional direction intersecting the optical axis, and the three-dimensional OCT data is obtained by a spot of the measurement light being caused by the scanning unit to scan in the two-dimensional measurement region.

3. The OCT data processing device according to claim 1, wherein when processing the OCT data newly obtained from the subject's eye for which the OCT data has been obtained in the past, the processor sets the same line pattern, with respect to the measurement region, as a line pattern set when processing the OCT data obtained in the past.

4. The OCT data processing device according to claim 3, wherein when processing the OCT data newly obtained from the subject's eye for which the OCT data has been obtained in the past, the processor sets the line pattern in the same position as a position at which a line pattern was set when processing the OCT data obtained in the past.

5. The OCT data processing device according to claim 1, wherein the processor determines a position at which the line pattern is set, based on a result of analysis processing performed on at least one of a two-dimensional front image of the measurement region or the three-dimensional OCT data obtained from the measurement region.

6. The OCT data processing device according to claim 1, wherein the processor is further programmed to:

create a line pattern in accordance with an operation command input from a user; and store information of the created line pattern in a memory as one of the plurality of types of line pattern.

7. The OCT data processing device according to claim 1, wherein the plurality of types of line pattern are stored in a memory, and the processor sets the line pattern by selecting, from among the plurality of types of line pattern stored in the memory, one or more line patterns.

8. The OCT data processing device according to claim 1, wherein the processor sets, from among the plurality of types of line pattern, a plurality of types of the line pattern.

9. A non-transitory computer-readable medium storing computer-readable instructions that, when executed by a processor of an optical coherence tomography (OCT) data processing device, cause the processor of the OCT data processing device to perform processes comprising:

acquiring three-dimensional OCT data, the three-dimensional OCT data being OCT data of a tissue of a subject's eye acquired by an OCT device, the OCT device comprises an OCT light source, a branching optical element, an irradiation optical system, a multiplexing optical element, and a photodetector, the branching optical element dividing light emitted from the OCT light source into measurement light and reference light, the irradiation optical system irradiating the measurement light divided by the branching optical element onto the tissue, the multiplexing optical element combining the measurement light reflected by the tissue and the reference light divided by the branching optical element and cause the measurement light and the reference light to interfere with each other, the photodetector detecting an interference signal by receiving interference light generated by the multiplexing optical element, the three-dimensional OCT data being three-dimensional OCT data obtained by irradiating the measurement light on a two-dimensional measurement region, the two-dimensional measurement region extending in a direction intersecting an optical axis of the measurement light;

setting a line pattern, from among a plurality of types of line pattern, with respect to the two-dimensional measurement region for which the three-dimensional OCT data is obtained, at least one of an arrangement, a number, or a shape of one or more lines being different for the plurality of types of line pattern; and extracting, from the three-dimensional OCT data, a two-dimensional tomographic image of a cross section intersecting each of the one or more lines of the set line pattern.

* * * * *